United States Patent
Relan et al.

(10) Patent No.: US 11,071,491 B2
(45) Date of Patent: Jul. 27, 2021

(54) METHODS AND SYSTEMS FOR MAPPING CARDIAC REPOLARIZATION

(71) Applicant: St. Jude Medical, Cardiology Division, Inc., St. Paul, MN (US)

(72) Inventors: Jatin S. Relan, Bordeaux (FR); Valtino X. Afonso, Oakdale, MN (US)

(73) Assignee: St. Jude Medical, Cardiology Division, Inc., St. Paul, MN (US)

(*) Notice: Subject to any disclaimer, the term of this patent is extended or adjusted under 35 U.S.C. 154(b) by 420 days.

(21) Appl. No.: 15/766,283

(22) PCT Filed: Sep. 29, 2016

(86) PCT No.: PCT/US2016/054280
§ 371 (c)(1),
(2) Date: Apr. 5, 2018

(87) PCT Pub. No.: WO2017/062247
PCT Pub. Date: Apr. 13, 2017

(65) Prior Publication Data
US 2018/0289276 A1 Oct. 11, 2018

Related U.S. Application Data

(60) Provisional application No. 62/238,323, filed on Oct. 7, 2015.

(51) Int. Cl.
*A61B 5/349* (2021.01)
*A61B 5/00* (2006.01)
*A61B 5/283* (2021.01)

(52) U.S. Cl.
CPC .............. *A61B 5/349* (2021.01); *A61B 5/283* (2021.01); *A61B 5/6852* (2013.01); *A61B 5/7239* (2013.01); *A61B 2505/05* (2013.01)

(58) Field of Classification Search
CPC ..... A61B 5/0452; A61B 5/042; A61B 5/6852; A61B 5/7239; A61B 2505/05
See application file for complete search history.

(56) References Cited

U.S. PATENT DOCUMENTS

| 5,423,878 A | 6/1995 | Franz |
| 5,697,377 A | 12/1997 | Wittkampf |

(Continued)

FOREIGN PATENT DOCUMENTS

| WO | 01/13992 | 3/2001 |
| WO | 2004/096354 | 11/2004 |

(Continued)

OTHER PUBLICATIONS

P. Colli Franzone et al. "Monophasic action potentials generated by bidomain modeling as a tool for detecting cardiac repolarization times," American Journal of Physiology: Heart and Circulatory Physiology, vol. 293, No. 5., dated Jan. 1, 2007.

(Continued)

*Primary Examiner* — Gary Jackson
*Assistant Examiner* — Jessandra F Hough
(74) *Attorney, Agent, or Firm* — Wiley Rein LLP (57) ABSTRACT

Cardiac repolarization activity can be mapped using action potential duration ("APD") and/or activation recovery interval ("ARI"). APD can be measured using a bipolar electrogram signal measured, for example, using a monophasic action potential ("MAP") catheter. ARI can be measured using unipolar electrogram signals. The electrogram signal is used to identify a depolarization tick time. A repolarization tick time can be identified using either a point in time when the electrogram signal passes below a threshold or via local maxima and minima of a first derivative of the electrogram signal. Diastolic intervals can also be computed using depolarization and repolarization tick times.

9 Claims, 6 Drawing Sheets

(56) References Cited

U.S. PATENT DOCUMENTS

| | | | |
|---|---|---|---|
| 5,983,126 A | 11/1999 | Wittkampf | |
| 6,640,119 B1 | 10/2003 | Budd et al. | |
| 6,728,562 B1 | 4/2004 | Budd et al. | |
| 6,939,309 B1 | 9/2005 | Beatty et al. | |
| 6,947,785 B1 | 9/2005 | Beatty et al. | |
| 6,978,168 B2 | 12/2005 | Beatty et al. | |
| 6,990,370 B1 | 1/2006 | Beatty et al. | |
| 7,263,397 B2 | 8/2007 | Hauck et al. | |
| 7,885,707 B2 | 2/2011 | Hauck | |
| 8,265,756 B1 * | 9/2012 | Snell | A61N 1/36507 600/509 |
| 2005/0261599 A1 * | 11/2005 | Shvilkin | A61B 5/0452 600/515 |
| 2008/0125665 A1 | 5/2008 | Nigam | |
| 2009/0299424 A1 | 12/2009 | Narayan | |
| 2010/0094274 A1 * | 4/2010 | Narayan | A61B 5/0245 606/33 |
| 2014/0187989 A1 | 7/2014 | Thakur et al. | |
| 2015/0342488 A1 * | 12/2015 | Laughner | A61B 5/361 600/523 |

FOREIGN PATENT DOCUMENTS

| | | |
|---|---|---|
| WO | 2008008361 | 1/2008 |
| WO | 2010/054409 | 5/2010 |

OTHER PUBLICATIONS

International Search Report and Written Opinion for PCT/US2016/054280, dated Jan. 3, 2017.

* cited by examiner

METHODS AND SYSTEMS FOR MAPPING CARDIAC REPOLARIZATION

CROSS-REFERENCE TO RELATED APPLICATIONS

This application claims the benefit of U.S. provisional application No. 62/238,323, filed 7 Oct. 2015, which is hereby incorporated by reference as though fully set forth herein.

BACKGROUND

The instant disclosure relates to electrophysiological mapping, such as may be performed in cardiac diagnostic and therapeutic procedures. In particular, the instant disclosure relates to systems, apparatuses, and methods for mapping cardiac repolarization activity, including action potential duration ("APD") and activation recovery interval ("ARI").

It is known to map cardiac depolarization activity, for example as part of an electrophysiology study. Cardiac repolarization activity, however, is not generally mapped during electrophysiology studies. One reason for this disparity is that depolarization wave potentials are typically stronger than repolarization wave potentials, increasing the complexity of mapping the repolarization activity.

Nonetheless, it can be desirable to map repolarization activity. For example, research suggests that repolarization plays a role in arrhythmogenesis, such that maps of repolarization activity might be of use in identifying better substrate for ablation therapy.

BRIEF SUMMARY

Disclosed herein is a method of mapping cardiac repolarization activity, including the following steps: receiving an electrogam signal S(t) at a signal processor; and using the signal processor: computing a second derivative S"(t) of the electrogram signal S(t) for a preset window about a reference time $T_{ref}$; identifying a depolarization tick time $T_D$ within the preset window using S"(t); identifying a repolarization tick time $T_R$ using S(t), wherein the repolarization tick time $T_R$ is identified as a point in time when S(t) passes below a preset threshold; and computing an action potential duration for the preset window using the depolarization tick time $T_D$ and the repolarization tick time $T_R$. It is contemplated that the electrogram signal S(t) can be a bipolar electrogram signal from a monophasic action potential ("MAP") catheter. It is also contemplated that the reference time $T_{ref}$ can be detected using a reference cardiac signal.

In embodiments, the step of computing a second derivative S"(t) of the electrogram S(t) for a preset window about a reference time $T_{ref}$ includes computing a first derivative S'(t) of the electrogram S(t) for the preset window about the reference time $T_{ref}$ according to a formula $$S'(t) = \frac{S(t + \Delta t) - S(t)}{\Delta t},$$

wherein $\Delta t$ comprises a preset time interval, such as about 3 ms.

According to aspects of the disclosure, the step of identifying a depolarization tick time $T_D$ within the preset window using S"(t) can include: identifying a time point within the preset window when S"(t) reaches its maximum; and designating the time point when S"(t) reaches its maximum as the depolarization tick time $T_D$.

The preset threshold can be computed as a function of an amplitude of S(t), such as 10% of the amplitude of S(t). In other embodiments, the preset threshold can be computed according to the following steps: identifying a maximum tick time $T_{max}$ and a minimum tick time $T_{min}$ within a preset refractory window surrounding the depolarization tick time $T_D$ using S(t); identifying an isopotential tick time $T_{iso}$ occurring before $T_{min}$ using S"(t); identifying a plateau tick time $T_{plateau}$ occurring after $T_{max}$ using a first derivative S'(t) of S(t); defining the amplitude A of S(t) as $S(T_{plateau})-S(T_{iso})$; and defining the preset threshold as $S(T_{plateau})-x*A$, $0<x<1$.

The method optionally also includes computing a diastolic interval for the preset window using the depolarization tick time $T_D$ within the preset window and an immediately previous repolarization tick time $T_{R-1}$.

In another embodiment of the disclosure, a method of mapping cardiac repolarization activity includes: receiving an electrogram signal S(t) at a signal processor; and using the signal processor: identifying a local activation time ("LAT") tick time within a preset window about a reference time $T_{ref}$; defining the LAT tick time as a depolarization tick time $T_D$ for the preset window; computing a first derivative S'(t) of the electrogram signal S(t) for the preset window; identifying a repolarization tick time $T_R$ using local maxima and local minima of S'(t); and computing an activation recovery interval for the preset window using the depolarization tick time $T_D$ and the repolarization tick time $T_R$. The electrogram signal S(t) can include a unipolar electrogram signal. In addition, the step of identifying a local activation time ("LAT") tick time within a preset window about a reference time $T_{ref}$ can include identifying the LAT tick time within the preset window about the reference time $T_{ref}$ using a bipolar electrogram signal.

In embodiments, the step of computing a first derivative S'(t) of the electrogram signal S(t) for the preset window includes computing the first derivative S'(t) according to a formula $$S'(t) = \frac{S(t + \Delta t) - S(t)}{\Delta t},$$

wherein $\Delta t$ comprises a preset time interval, such as about 3 ms.

According to aspects of the disclosure, the step of identifying a repolarization tick time $T_R$ using local maxima and local minima of S'(t) includes: identifying a maximum tick time $T_{max}$ and a minimum tick time $T_{min}$ within a preset refractory window $\Delta RW$ surrounding the depolarization tick time $T_D$ using S(t); computing a LAT amplitude $L_1$ using $S(T_{max})$ and $S(T_{min})$; identifying a next cycle tick $T_{next}$ occurring after $T_{max}$ using S(t); determining a search period following the depolarization tick time $T_D$ for the repolarization tick time $T_R$; identifying a time $T_{SLM}$ during the search period at which S'(t) reaches a local maximum; identifying a time $T_{slm}$ during the search period at which S'(t) reaches a local minimum; and defining the repolarization tick time $T_R$ using one or more of $T_{SLM}$ and $T_{slm}$.

Further, it is contemplated that the step of identifying a next cycle tick $T_{next}$ occurring after $T_{max}$ using S(t) can include: defining a local minimum threshold higher than $S(T_{min})$; defining a local maximum threshold higher than $S(T_{max})$; analyzing $S(t)$ after $T_{max}$; and identifying $T_{next}$ as a first to occur of: a time at which $S(t)$ drops below the local minimum threshold; a time at which $S(t)$ exceeds the local maximum threshold; and a time at which $S(t)$ ends. The local minimum threshold can be computed as $S(T_{min})+0.3*L_1$; and the local maximum threshold can be computed as $S(T_{max})+0.3*L_1$.

According to aspects of the disclosure, the step of determining a search period following the depolarization tick time $T_D$ for the repolarization tick time $T_R$ includes: computing a search interval $L_2$ as $T_{next}-T_D-2(\Delta RW)$; defining a start of the search period at $T_D+\Delta RW$; and defining an end of the search period at $T_D+\Delta RW+0.75*L_2$.

According to additional aspects of the disclosure, the step of defining the repolarization tick time $T_R$ using one or more of $T_{SLM}$ and $T_{slm}$ includes: defining $T_R$ as $$\min(T_{SLM}, T_{slm}) + \frac{T_{SLM} + T_{slm}}{2}$$

for a biphasic T-wave; defining $T_R$ as $T_{SLM}$ for a negative T-wave; and defining $T_R$ as $T_{slm}$ for a positive T-wave.

The method optionally includes computing a diastolic interval for the preset window using the depolarization tick time $T_D$ for the preset window and an immediately previous repolarization tick time $T_{R-1}$.

Also disclosed herein is a system for mapping cardiac repolarization activity. The system includes: a cardiac repolarization detection processor configured: to receive an electrogram $S(t)$; to identify a depolarization tick time $T_D$ using the electrogram $S(t)$; to identify a repolarization tick time $T_R$ using either a point in time when $S(t)$ passes below a preset threshold or local maxima and local minima of a first derivative $S'(t)$ of the electrogram $S(t)$; and to compute a cardiac repolarization time period using the depolarization tick time $T_D$ and the repolarization tick time $T_R$. The cardiac repolarization detection processor can also be configured to compute a diastolic interval using the depolarization tick time $T_D$ and a an immediately previous repolarization tick time $T_{R-1}$. The repolarization time period can be an action potential duration and/or an activation recovery interval.

The foregoing and other aspects, features, details, utilities, and advantages of the present invention will be apparent from reading the following description and claims, and from reviewing the accompanying drawings.

DETAILED DESCRIPTION

The present disclosure provides methods, apparatuses, and systems for the creation of electrophysiology maps (e.g., electrocardiographic maps) that provide information regarding cardiac repolarization activity. Certain embodiments of the disclosure will be explained with reference to the use of bipolar electrograms, such as measured by a MAP catheter, to determine APD. Other embodiments of the disclosure will be explained with reference to the use of unipolar electrograms to determine ARI. It should be understood, however, that the teachings herein can be applied to good advantage in other contexts, such as mapping local electrogram QRS activity width, which can be representative of the pattern of wave conduction.

Figure 1:
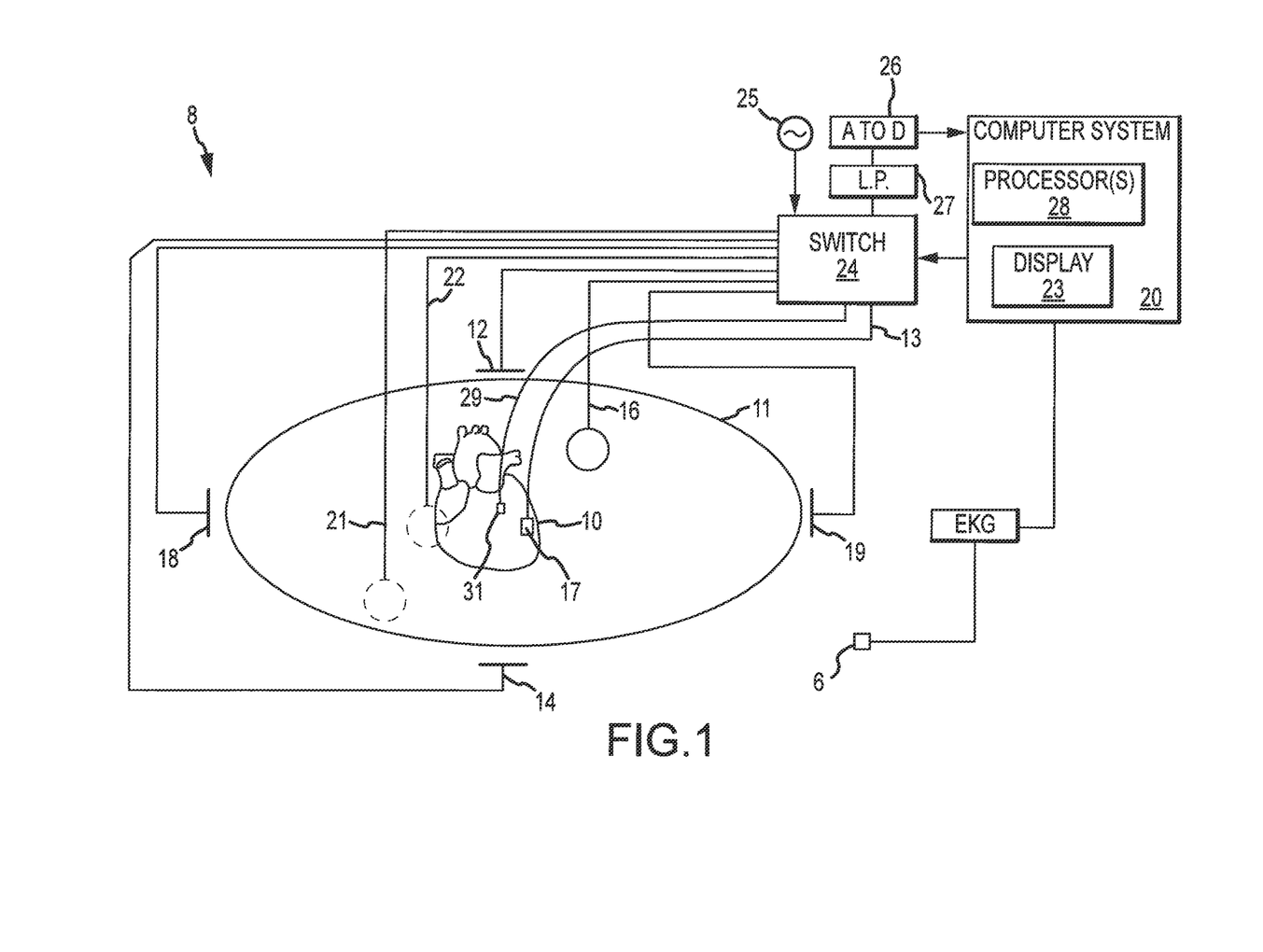
FIG. 1 is a schematic of an electrophysiology system, such as may be used in an electrophysiology study including mapping cardiac repolarization activity.

FIG. 1 shows a schematic diagram of an electrophysiology system 8 for conducting cardiac electrophysiology studies by navigating a cardiac catheter and measuring electrical activity occurring in a heart 10 of a patient 11 and three-dimensionally mapping the electrical activity and/or information related to or representative of the electrical activity so measured. System 8 can be used, for example, to create an anatomical model of the patient's heart 10 using one or more electrodes. System 8 can also be used to measure electrophysiology data, including, but not limited to, electrical activation data (e.g., local activation time ("LAT")), at a plurality of points along a cardiac surface and store the measured data in association with location information for each measurement point at which the electrophysiology data was measured, for example to create an electrophysiology map of the patient's heart 10 (or a portion thereof).

As one of ordinary skill in the art will recognize, and as will be further described below, system 8 can determine the location, and in some aspects the orientation, of objects, typically within a three-dimensional space, and express those locations as position information determined relative to at least one reference.

For simplicity of illustration, the patient 11 is depicted schematically as an oval. In the embodiment shown in FIG. 1, three sets of surface electrodes (e.g., patch electrodes) are shown applied to a surface of the patient 11, defining three generally orthogonal axes, referred to herein as an x-axis, a y-axis, and a z-axis. In other embodiments the electrodes could be positioned in other arrangements, for example multiple electrodes on a particular body surface. As a further alternative, the electrodes do not need to be on the body surface, but could be positioned internally to the body or on an external frame.

In FIG. 1, the x-axis surface electrodes 12, 14 are applied to the patient along a first axis, such as on the lateral sides of the thorax region of the patient (e.g., applied to the patient's skin underneath each arm) and may be referred to as the Left and Right electrodes. The y-axis electrodes 18, 19 are applied to the patient along a second axis generally orthogonal to the x-axis, such as along the inner thigh and neck regions of the patient, and may be referred to as the Left Leg and Neck electrodes. The z-axis electrodes 16, 22 are applied along a third axis generally orthogonal to both the x-axis and the y-axis, such as along the sternum and spine of the patient in the thorax region, and may be referred to as the Chest and Back electrodes. The heart 10 lies between these pairs of surface electrodes 12/14, 18/19, and 16/22.

An additional surface reference electrode (e.g., a "belly patch") 21 provides a reference and/or ground electrode for the system 8. The belly patch electrode 21 may be an alternative to a fixed intra-cardiac electrode 31, described in further detail below. It should also be appreciated that, in addition, the patient 11 may have most or all of the conventional electrocardiogram ("ECG" or "EKG") system leads in place. In certain embodiments, for example, a standard set of 12 ECG leads may be utilized for sensing electrocardiograms on the patient's heart 10. This ECG information is available to the system 8 (e.g., it can be provided as input to computer system 20). Insofar as ECG leads are well understood, and for the sake of clarity in the figures, only one lead 6 and its connection to computer system 20 is illustrated in FIG. 1.

A representative catheter 13 having at least one electrode 17 (e.g., a distal electrode) is also depicted in schematic fashion in FIG. 1. This representative catheter electrode 17 can be referred to as a "measurement electrode" or a "roving electrode." Typically, multiple electrodes on catheter 13, or on multiple such catheters, will be used. In one embodiment, for example, system 8 may utilize sixty-four electrodes on twelve catheters disposed within the heart and/or vasculature of the patient.

In other embodiments, system 8 may utilize a single catheter that includes multiple (e.g., eight) splines, each of which in turn includes multiple (e.g., eight) electrodes. Of course, these embodiments are merely exemplary, and any number of electrodes and catheters may be used. Indeed, in some embodiments, a high density mapping catheter, such as the EnSite™ Array™ non-contact mapping catheter of St. Jude Medical, Inc., can be utilized.

Figure 2:
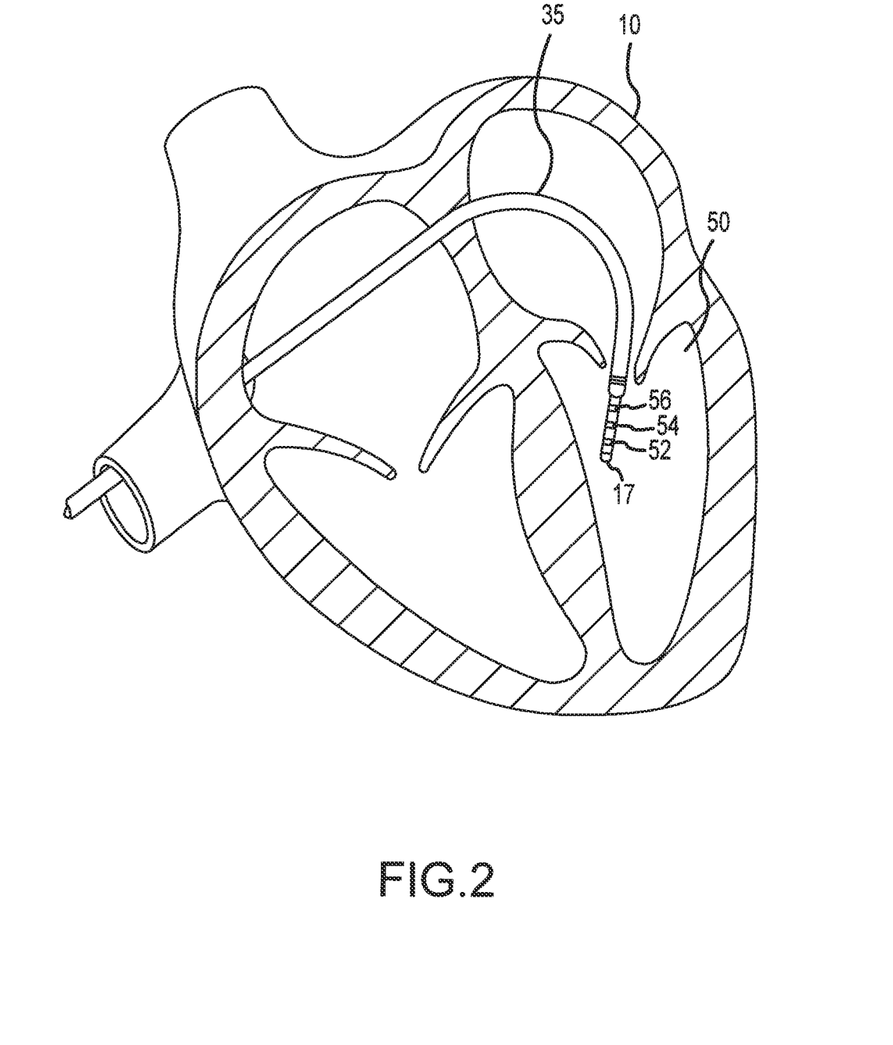
FIG. 2 depicts an exemplary multi-electrode catheter used in an electrophysiology study.

Likewise, it should be understood that catheter 13 (or multiple such catheters) are typically introduced into the heart and/or vasculature of the patient via one or more introducers and using familiar procedures. For purposes of this disclosure, a segment of an exemplary multi-electrode catheter 13 is shown in FIG. 2. In FIG. 2, catheter 13 extends into the left ventricle 50 of the patient's heart 10 through a transseptal sheath 35. The use of a transseptal approach to the left ventricle is well known and will be familiar to those of ordinary skill in the art, and need not be further described herein. Of course, catheter 13 can also be introduced into the heart 10 in any other suitable manner.

Catheter 13 includes electrode 17 on its distal tip, as well as a plurality of additional measurement electrodes 52, 54, 56 spaced along its length in the illustrated embodiment. Typically, the spacing between adjacent electrodes will be known, though it should be understood that the electrodes may not be evenly spaced along catheter 13 or of equal size to each other. Since each of these electrodes 17, 52, 54, 56 lies within the patient, location data may be collected simultaneously for each of the electrodes by system 8.

Similarly, each of electrodes 17, 52, 54, and 56 can be used to gather electrophysiological data from the cardiac surface. For example, in some embodiments, catheter 13 is capable of sensing MAPs (e.g., from bipolar electrograms). The ordinarily skilled artisan will be familiar with various modalities for the acquisition and processing of electrophysiology data points (including, for example, both contact and non-contact electrophysiological mapping and the collection of both unipolar and bipolar electrograms), such that further discussion thereof is not necessary to the understanding of the cardiac repolarization activity mapping techniques disclosed herein. Likewise, various techniques familiar in the art can be used to generate a graphical representation from the plurality of electrophysiology data points. Insofar as the ordinarily skilled artisan will appreciate how to create electrophysiology maps from electrophysiology data points, the aspects thereof will only be described herein to the extent necessary to understand the maps disclosed herein.

Returning now to FIG. 1, in some embodiments, a fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrodes (e.g., electrodes 17, 52, 54, 56), and thus may be referred to as a "navigational reference" or "local reference." The fixed reference electrode 31 may be used in addition or alternatively to the surface reference electrode 21 described above. In many instances, a coronary sinus electrode or other fixed electrode in the heart 10 can be used as a reference for measuring voltages and displacements; that is, as described below, fixed reference electrode 31 may define the origin of a coordinate system.

Each surface electrode is coupled to a multiplex switch 24, and the pairs of surface electrodes are selected by software running on a computer 20, which couples the surface electrodes to a signal generator 25. Alternately, switch 24 may be eliminated and multiple (e.g., three) instances of signal generator 25 may be provided, one for each measurement axis (that is, each surface electrode pairing).

The computer 20, for example, may comprise a conventional general-purpose computer, a special-purpose computer, a distributed computer, or any other type of computer. The computer 20 may comprise one or more processors 28, such as a single central processing unit (CPU), or a plurality of processing units, commonly referred to as a parallel processing environment, which may execute instructions to practice the various aspects disclosed herein.

Generally, three nominally orthogonal electric fields are generated by a series of driven and sensed electric dipoles (e.g., surface electrode pairs 12/14, 18/19, and 16/22) in order to realize catheter navigation in a biological conductor. Alternatively, these orthogonal fields can be decomposed and any pairs of surface electrodes can be driven as dipoles to provide effective electrode triangulation. Likewise, the electrodes 12, 14, 18, 19, 16, and 22 (or any other number of electrodes) could be positioned in any other effective arrangement for driving a current to or sensing a current from an electrode in the heart. For example, multiple electrodes could be placed on the back, sides, and/or belly of patient 11. For any desired axis, the potentials measured across the roving electrodes resulting from a predetermined set of drive (source-sink) configurations may be combined algebraically to yield the same effective potential as would be obtained by simply driving a uniform current along the orthogonal axes.

Thus, any two of the surface electrodes 12, 14, 16, 18, 19, 22 may be selected as a dipole source and drain with respect to a ground reference, such as belly patch 21, while the unexcited electrodes measure voltage with respect to the ground reference. The roving electrodes 17, 52, 54, 56 placed in the heart 10 are exposed to the field from a current pulse and are measured with respect to ground, such as belly patch 21. In practice the catheters within the heart 10 may contain more or fewer electrodes than the four shown, and each electrode potential may be measured. As previously noted, at least one electrode may be fixed to the interior surface of the heart to form a fixed reference electrode 31, which is also measured with respect to ground, such as belly patch 21, and which may be defined as the origin of the coordinate system relative to which localization system 8 measures positions. Data sets from each of the surface electrodes, the internal electrodes, and the virtual electrodes may all be used to determine the location of the roving electrodes 17, 52, 54, 56 within heart 10.

The measured voltages may be used by system 8 to determine the location in three-dimensional space of the electrodes inside the heart, such as roving electrodes 17, 52, 54, 56, relative to a reference location, such as reference electrode 31. That is, the voltages measured at reference electrode 31 may be used to define the origin of a coordinate system, while the voltages measured at roving electrodes 17, 52, 54, 56 may be used to express the location of roving electrodes 17, 52, 54, 56 relative to the origin. In some embodiments, the coordinate system is a three-dimensional (x, y, z) Cartesian coordinate system, although other coordinate systems, such as polar, spherical, and cylindrical coordinate systems, are contemplated.

As should be clear from the foregoing discussion, the data used to determine the location of the electrode(s) within the heart is measured while the surface electrode pairs impress an electric field on the heart. The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

In one representative embodiment, the system 8 first selects a set of surface electrodes and then drives them with current pulses. While the current pulses are being delivered, electrical activity, such as the voltages measured with at least one of the remaining surface electrodes and in vivo electrodes, is measured and stored. Compensation for artifacts, such as respiration and/or impedance shifting, may be performed as indicated above.

In some embodiments, system 8 is the EnSite™ Velocity™ cardiac mapping and visualization system of St. Jude Medical, Inc., which generates electrical fields as described above, or another such system that relies upon electrical fields. Other systems, however, may be used in connection with the present teachings, including for example, the CARTO navigation and location system of Biosense Webster, Inc., the AURORA® system of Northern Digital Inc., or Sterotaxis' NIOBE® Magnetic Navigation System, all of Which utilize magnetic fields rather than electrical fields. The localization and mapping systems described in the following patents (all of which are hereby incorporated by reference in their entireties) can also be used with the present invention: U.S. Pat. Nos. 6,990,370; 6,978,168; 6,947,785; 6,939,309; 6,728,562; 6,640,119; 5,983,126; and 5,697,377.

One basic methodology of mapping cardiac repolarization activity will be explained with reference to the flowchart 300 of representative steps presented as FIG. 3. In some embodiments, for example, flowchart 300 may represent several exemplary steps that can be carried out by the computer 20 of FIG. 1 (e.g., by one or more processors 28) to generate a map of cardiac repolarization activity as described herein. It should be understood that the representative steps described below can be either hardware- or software-implemented. For the sake of explanation, the term "signal processor" is used herein to describe both hardware- and software-based implementations of the teachings herein.

Figure 3:
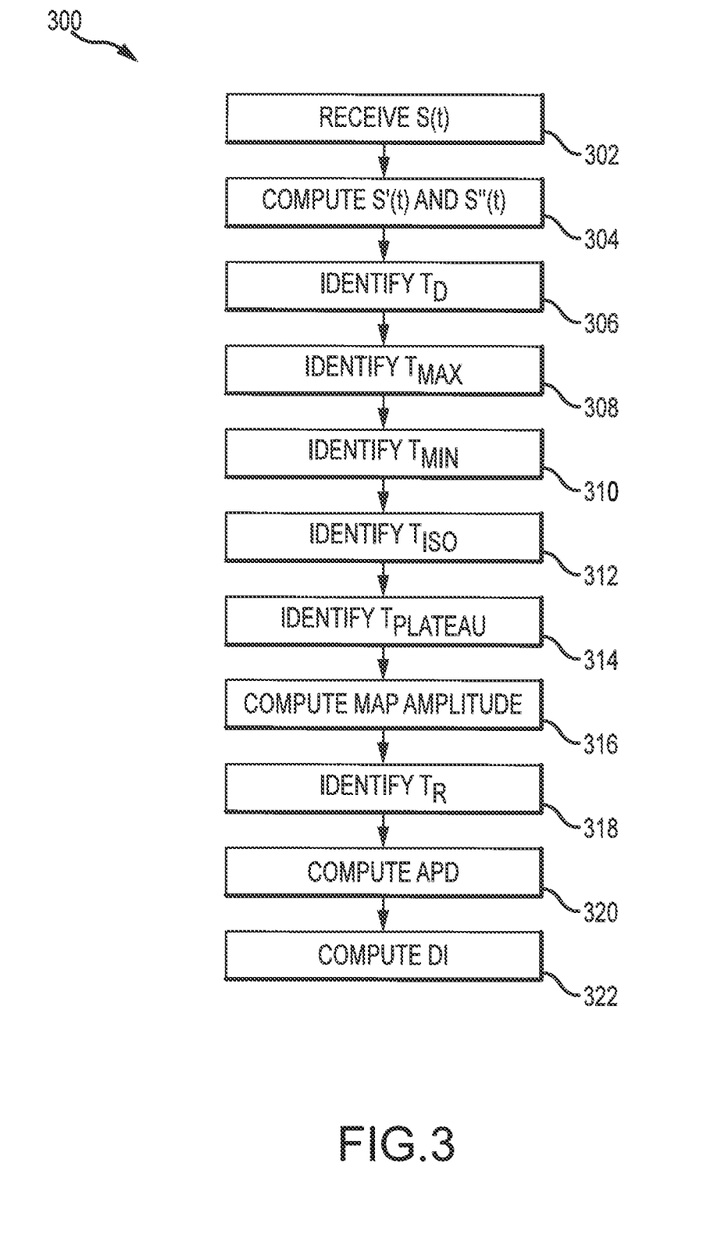
FIG. 3 is a flowchart of representative steps that can be followed to map cardiac repolarization activity using a monophasic action potential ("MAP") catheter to determine action potential duration ("APD").

More particularly, flowchart 300 in FIG. 3 illustrates a series of representative steps that may be carried out to map cardiac repolarization activity using APD. In step 302, an electrogram signal, denoted S(t) (and illustrated as lower trace 402 in FIG. 4), is received at a signal processor (e.g., by one or more processors 28 within computer 20). For mapping APD, it is desirable that the electrogram signal 402 be a bipolar electrogram signal, such as from a MAP catheter (see, e.g., U.S. Pat. No. 5,398,683, which is hereby incorporated by reference as though fully set forth herein).

In block 304, the first and second derivatives of S(t), denoted S'(t) and S"(t), respectively, are computed. In embodiments, the first derivative Sit) is calculated using the formula $$S'(t) = \frac{S(t + \Delta t) - S(t)}{\Delta t},$$

where Δt is a preset time interval, such as 3 ms. Similarly, the second derivative S"(t) can be computed according to the formula $$S''(t) = \frac{S'(t + \Delta t) - S'(t)}{\Delta t}.$$

Figure 4:
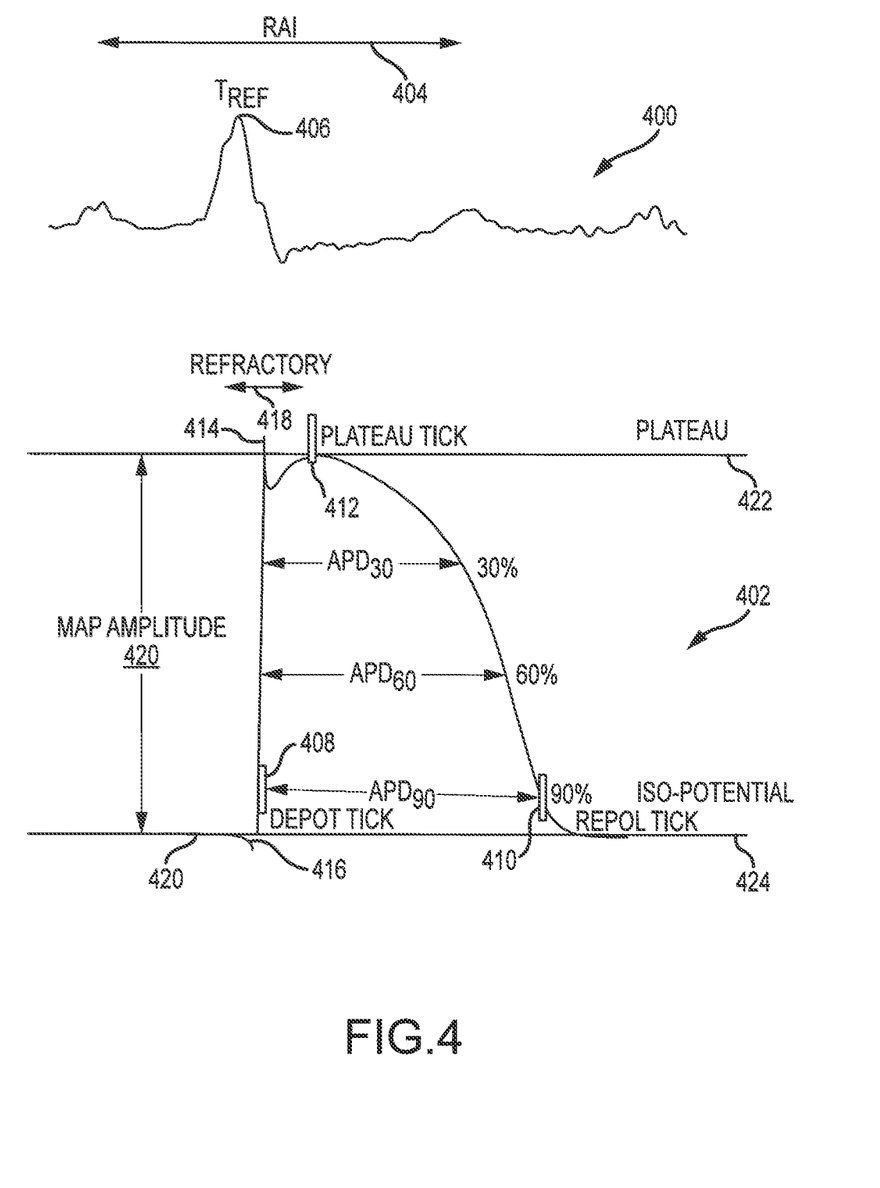
FIG. 4 is a representation of cardiac electrical activity with various tick times and other values referenced in the flowchart of FIG. 3 annotated thereon.

More specifically, S'(t) and S"(t) are computed for a preset window, referred to herein as a "Roving Activation Interval" ("RAI") 404, about a reference time point 406, denoted $T_{ref}$, in block 304. According to aspects disclosed herein, $T_{ref}$ 406 is set to correspond to QRS activity detected using a user-defined reference cardiac signal, such as the signal from an EKG lead or the signal from an in vivo reference electrode. The upper trace 400 in FIG. 4 is a representative reference cardiac signal, such as may be used to determine $T_{ref}$ 406.

Likewise, the width of RAI 404 can be user-defined. According to aspects of the disclosure, RAI 404 is between about 100 ms and about 300 ms wide.

In block 306, a depolarization tick time 408, denoted $T_D$, is identified within the RAI using S"(t). For example, $T_D$ 408 can be designated as the time point within RAI 404 where S"(t) reaches its maximum.

The next several steps illustrated in FIG. 3 are directed at identifying a repolarization tick time 410, denoted $T_R$, for the current cardiac trigger (that is, the current beat). It should be understood that the repolarization tick time 410 for the current cardiac trigger need not occur within RAI 404. Rather, according to some aspects of the disclosure, the repolarization tick time 410 can be identified within a user-defined minimum cycle length threshold ("$CL_{min}$") of $T_{plateau}$ 412 (described further below). In any event, however, $T_R$ 410 is typically identified as a point in time where S(t) 402 passes below a preset threshold, as further described below.

In blocks 308 and 310 respectively, a maximum tick time 414 (denoted $T_{max}$) and a minimum tick time 416 (denoted $T_{min}$) are identified within a preset refractory window 418 (denoted ΔRW) of $T_D$ 408. $T_{max}$ 414 is the time point, within the refractory window 418, at which S(t) 402 achieves its local maximum; conversely, $T_{min}$ 416 is the time point, within the refractory window 418, at which S(t) 402 achieves its local minimum.

In embodiments, the preset refractory window 418 is 12 ms to either side of the depolarization tick time 408 (i.e., $T_D\pm12$ ms). The teachings herein are not limited, however, to this specific refractory window, and other refractory windows, including refractory windows that are not centered on the depolarization tick time 408, can be employed without departing from the scope of the teachings herein.

An isopotential tick time 420, denoted $T_{iso}$, is detected in block 312. According to aspects of the disclosure, the isopotential tick time 420 is detected as a time point before the minimum tick time 416 at which the absolute value of S"(t) drops below a preset threshold, such as 0.01. If no such point exists, then flowchart 300 can terminate for the current beat.

Similarly, in block 314, a plateau tick time 412 ($T_{plateau}$) is detected. According to aspects of the disclosure, the plateau tick time 412 is detected as a time point after the maximum tick time 414 at which the absolute value of S'(t) goes below a preset threshold, such as 0.5. If no such point exists, then flowchart 300 can terminate for the current beat.

In block 316, a MAP amplitude 420 (represented by the letter A in this disclosure and shown as "MAP amplitude" in FIG. 4) is computed as the difference between $S(T_{plateau})$ 422 and $S(T_{iso})$ 424. The MAP amplitude 420 is used to determine the preset threshold that will be used to determine the repolarization tick time 410 (block 318), for example by setting the preset threshold as a fraction of the MAP amplitude 420. In embodiments disclosed herein, the preset threshold is set at 10% of the MAP amplitude 420 (that is, the repolarization tick time is detected when S(t) drops below $S(T_{plateau})-0.9(A)$). If no such point exists within the minimum cycle length threshold of the plateau tick time 412 (that is, if the amplitude of S(t) 402 does not diminish sufficiently within a preset time of when it plateaus), then flowchart 300 can terminate for the current beat.

Once the repolarization tick time 410 is detected, APD can be computed as the difference between the depolarization and repolarization tick times 408, 410 respectively (block 320). In addition, a diastolic interval can be computed as the difference between the depolarization tick time and an immediately previous repolarization tick time (i.e., $T_{R-1}$).

Another basic methodology of mapping cardiac repolarization activity will be explained with reference to the flowchart 500 of representative steps presented as FIG. 5. That is, flowchart 500 may represent several exemplary steps that can be carried out by the computer 20 of FIG. 1 (e.g. by one or more processors 28) to generate a map of cardiac repolarization activity as described herein. Once again, it should be understood that the representative steps described below can be either hardware- or software-implemented, and the term "signal processor" will again be used to describe both hardware- and software-based implementations of the teachings herein.

Figure 5:
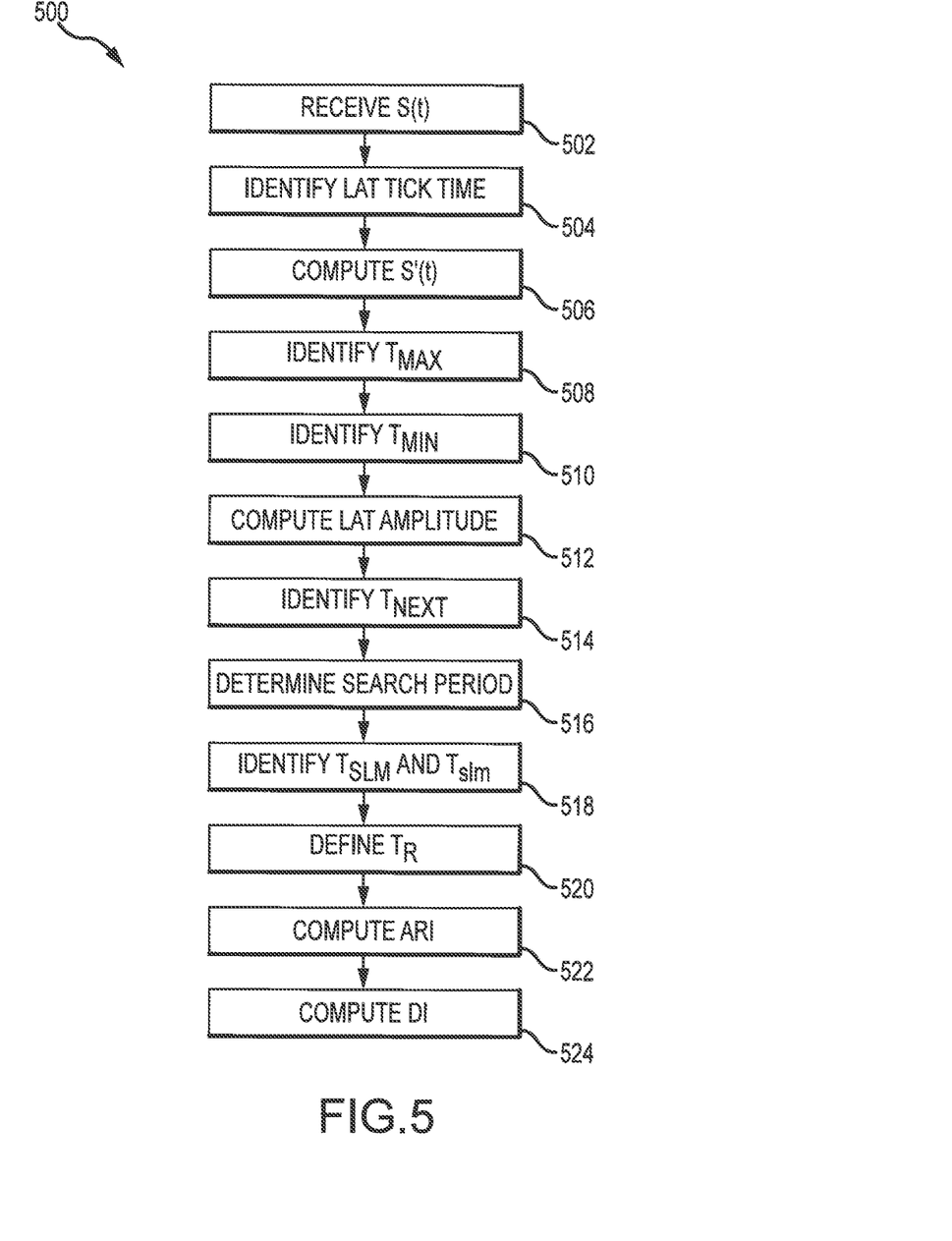
FIG. 5 is a flowchart of representative steps that can be followed to map cardiac repolarization activity using unipolar electrograms ("EGMs") to determine activation recovery interval ("ARI").
Figure 6:
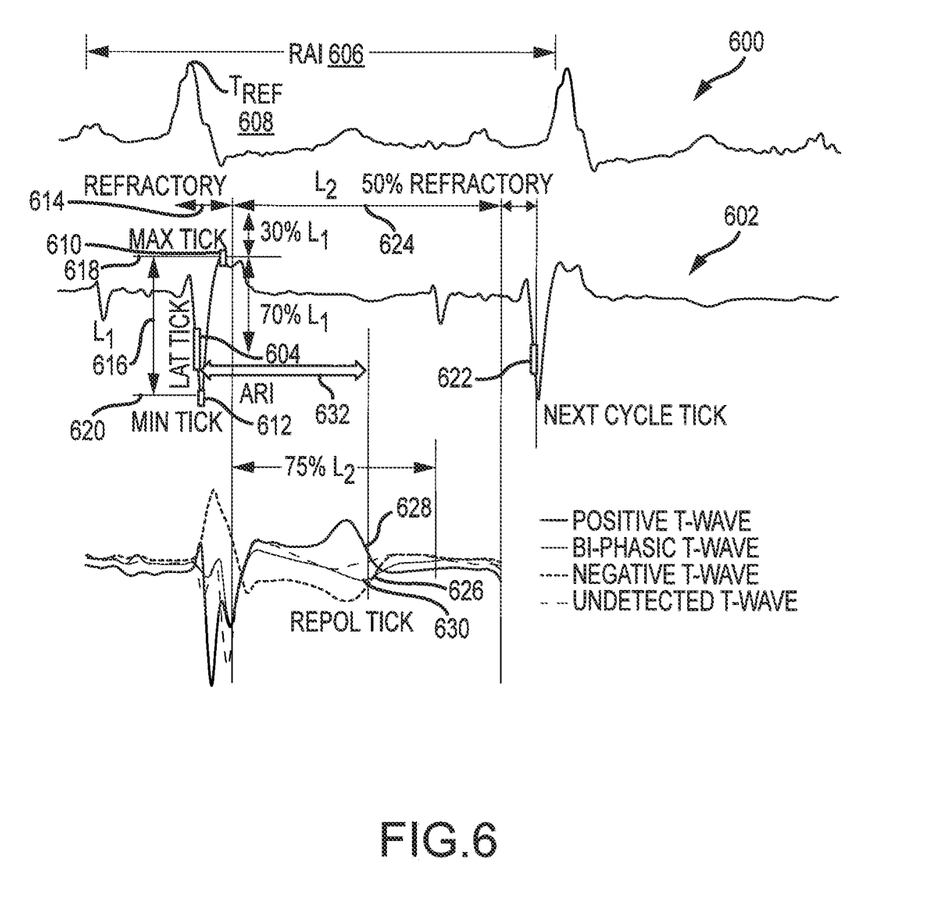
FIG. 6 is a representation of cardiac electrical activity with various tick times and other values referenced in the flowchart of FIG. 5 annotated thereon.

More particularly, flowchart 500 in FIG. 5 illustrates a series of representative steps that may be carried out to map cardiac repolarization activity using ARI. In step 502, an electrogram signal, again denoted S(t) and illustrated as lower trace 602 in FIG. 6, is received at a signal processor (e.g., by one or more processors 28 within computer 20). For mapping ARI, it is desirable that the electrogram signal be a unipolar electrogram signal.

In block 504, a local activation time ("LAT") tick time 604 is identified within a preset window, again referred to as a "Roving Activation Interval" ("RAI") 606, about a reference time point $T_{ref}$ 608. Similar to trace 400 in FIG. 4, the upper trace 600 in FIG. 6 is a representative reference cardiac signal, such as may be used to identify $T_{ref}$ 608. In embodiments of the disclosure, the LAT tick time 604 is identified using a bipolar electrogram signal 602. Once identified, the LAT tick time 604 is defined as the depolarization tick time $T_D$ for the RAI 606.

In block 506, the first derivative S'(t) of SW 602 is computed. As described in connection with FIG. 3, S'(t) can be computed as $$S'(t) = \frac{S(t+\Delta t) - S(t)}{\Delta t},$$

where $\Delta t$ is a preset time interval, such as 3 ms.

The next several steps illustrated in FIG. 5 are directed at identifying a repolarization tick time $T_R$ for the current cardiac trigger (that is, the current beat). It should be understood that the repolarization tick time for the current cardiac trigger need not occur within the RAI 606. Rather, as described below, a search period following the depolarization tick time 604 is defined, and the repolarization tick time is detected within this search period. In any event, however, $T_R$ is typically identified using local maxima and local minima of S'(t), as described in further detail below.

In blocks 508 and 510 respectively, a maximum tick time 610 (denoted $T_{max}$) and a minimum tick time 612 (denoted $T_{min}$) are identified within a preset refractory window 614 (denoted $\Delta RW$) of $T_D$ 604. $T_{max}$ 610 is the time point, within the refractory window 614, at Which S(t) 602 achieves its local maximum; conversely. $T_{min}$ 612 is the time point, within the refractory window 614, at which S(t) 602 achieves its local minimum.

In embodiments, the preset refractory window 614 is 50 ms to either side of the depolarization tick time 604 (i.e., $T_D\pm50$ ms). The teachings herein are not limited, however, to this specific refractory window, and other refractory windows, including refractory windows that are not centered on the depolarization tick time 604, can be employed without departing from the spirit of the teachings herein. A LAT amplitude 616 ($L_1$) is computed as the difference between $S(T_{max})$ 618 and $S(T_{min})$ 620 in block 512.

A next cycle tick time $T_{next}$ 622 is identified in block 514. It is contemplated that $T_{next}$ 622 can be identified with reference to a local minimum threshold, which is higher than $S(T_{min})$ 620, and a local maximum threshold, which is higher than $S(T_{max})$ 618.

The LAT amplitude 616 can be used to compute the local minimum and local maximum thresholds. For example, the local minimum threshold can Be computed as $S(T_{min})+0.3*L_1$, and the local maximum threshold can be computed as $S(T_{max})+0.3*L_1$.

In aspects of the disclosure, $T_{next}$ 622 is designated as the time point at which the first of the following occurs after $T_{max}$ 610: (1) S(t) 602 drops below the local minimum threshold; (2) S(t) 602 exceeds the local maximum threshold; or (3) S(t) 602 ends.

A search period, following the depolarization tick time 604, for the repolarization tick time is determined in block 516. In certain embodiments, the search period begins at $T_D+\Delta RW$ and ends at $TD+\Delta RW+0.75(L_2)$, where $L_2$ (624) is a search interval defined as $T_{next}-T_D-2(\Delta RW)$.

In block 518, two additional tick times are identified: $T_{SLM}$ and $T_{slm}$. $T_{SLM}$ is the time point during the search period at which S'(t) reaches a local maximum, while $T_{slm}$ is the time point during the search period at which S'(t) reaches a local minimum.

In block 520, the repolarization tick time is defined using one or more of $T_{SLM}$ and $T_{slm}$. According to aspects of the instant disclosure, the definition of the repolarization tick time depends on whether the T-wave is biphasic, negative, or positive. Thus, for example, the repolarization tick time can be defined as $T_{SLM}$ 626 for a negative T-wave and as $T_{slm}$ 628 for a positive T-wave. For a biphasic T-wave, the repolarization tick time 630 can be defined using the formula $$\min(T_{SLM}, T_{slm}) + \frac{T_{SLM} + T_{slm}}{2}.$$

Once the repolarization tick time is defined, ART 632 can be computed (block 522) as the difference between the depolarization and repolarization tick times. In addition, a diastolic interval can be computed (block 524) as the difference between the depolarization tick time and an immediately previous repolarization tick time $T_{R-1}$).

Although several embodiments of this invention have been described above with a certain degree of particularity, those skilled in the art could make numerous alterations to the disclosed embodiments without departing from the spirit or scope of this invention.

All directional references (e.g., upper, lower, upward, downward, left, right, leftward, rightward, top, bottom, above, below, vertical, horizontal, clockwise, and counter-clockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:

1. A method of mapping cardiac repolarization activity, comprising:
   receiving a unipolar electrogram signal S(t) at a signal processor; and
   using the signal processor:
      identifying a local activation time ("LAT") tick time within a preset window about a reference time $T_{ref}$;
      defining the LAT tick time as a depolarization tick time $T_D$ for the preset window;
      computing a first derivative S'(t) of the electrogram signal S(t) for the preset window;
      identifying a repolarization tick time $T_R$ using local maxima and local minima of S'(t); and
      computing an activation recovery interval for the preset window using the depolarization tick time $T_D$ and the repolarization tick time $T_R$,
   wherein identifying a repolarization tick time $T_R$ using local maxima and local minima of S'(t) comprises:
      identifying a maximum tick time $T_{max}$ and a minimum tick time $T_{min}$ within a preset refractory window $\Delta$RW surrounding the depolarization tick time $T_D$ using S(t);
      computing a LAT amplitude $L_1$ using $S(T_{max})$ and $S(T_{min})$;
      identifying a next cycle tick $T_{next}$ occurring after $T_{max}$ using S(t);
      determining a search period following the depolarization tick time $T_D$ for the repolarization tick time $T_R$;
      identifying a time $T_{SLM}$ during the search period at which S'(t) reaches a local maximum;
      identifying a time $T_{slm}$ during the search period at which S'(t) reaches a local minimum; and
      defining the repolarization tick time $T_R$ using one or more of $T_{SLM}$ and $T_{slm}$.

2. The method according to claim 1, wherein computing a first derivative S'(t) of the electrogram signal S(t) for the preset window comprises computing the first derivative S'(t) according to a formula $$S'(t) = \frac{S(t + \Delta t) - S(t)}{\Delta t},$$

wherein $\Delta t$ comprises a preset time interval.

3. The method according to claim 1, wherein identifying a next cycle tick $T_{next}$ occurring after $T_{max}$ using S(t) comprises:
   defining a local minimum threshold higher than $S(T_{min})$;
   defining a local maximum threshold higher than $S(T_{max})$;
   analyzing S(t) after $T_{max}$; and
   identifying $T_{next}$ as a first to occur of:
      a time at which S(t) drops below the local minimum threshold;
      a time at which S(t) exceeds the local maximum threshold; and
      a time at which S(t) ends.

4. The method according to claim 3, wherein:
   the local minimum threshold is computed as $S(T_{min})+ 0.3*L_1$; and
   the local maximum threshold is computed as $S(T_{max})+ 0.3*L_1$.

5. The method according to claim 1, wherein determining a search period following the depolarization tick time $T_D$ for the repolarization tick time $T_R$ comprises:
   computing a search interval $L_2$ as $T_{next}$ $T_D$ 2($\Delta$RW);
   defining a start of the search period at $T_D+\Delta$RW; and
   defining an end of the search period at $T_D$ $\Delta$RW+0.75*$L_2$.

6. The method according to claim 1, wherein defining the repolarization tick time $T_R$ using one or more of $T_{SLM}$ and $T_{slm}$ comprises:
   defining $T_R$ as $$\min(T_{SLM}, T_{slm}) + \frac{T_{SLM} + T_{slm}}{2}$$

for a biphasic T-wave;
   defining $T_R$ as $T_{SLM}$ for a negative T-wave; and
   defining $T_R$ as $T_{slm}$ for a positive T-wave.

7. The method according to claim 1, further comprising computing a diastolic interval for the preset window using the depolarization tick time $T_D$ for the preset window and an immediately previous repolarization tick time $T_{R-1}$.

8. A system for mapping cardiac repolarization activity, comprising:
   a cardiac repolarization detection processor configured:
      to receive a unipolar electrogram S(t);

to identify a local activation time ("LAT") tick time within a preset window about a reference time Tier and define the LAT tick time as a depolarization tick time $T_D$ for the preset window;

to compute a first derivative $S'(t)$ of the electrogram $S(t)$ for the preset window;

to identify a repolarization tick time $T_R$ using local maxima and local minima of the first derivative $S'(t)$ of the electrogram $S(t)$ by executing a process comprising:

identifying a maximum tick time $T_{max}$ and a minimum tick time $T_{min}$ within a preset refractory window $\Delta RW$ surrounding the depolarization tick time $T_D$ using $S(t)$;

computing a LAT amplitude $L_1$ using $S(T_{max})$ and $S(T_{min})$;

identifying a next cycle tick Text occurring after $T_{max}$ using $S(t)$;

determining a search period following the depolarization tick time $T_D$ for the repolarization tick time $T_R$;

identifying a time $T_{SLM}$ during the search period at which $S'(t)$ reaches a local maximum;

identifying a time $T_{slm}$ during the search period at which $S'(t)$ reaches a local minimum; and defining the repolarization tick time $T_R$ using one or more of $T_{SLM}$ and $T_{slm}$; and to compute an activation recovery interval using the depolarization tick time $T_D$ and the repolarization tick time $T_R$.

9. The system according to claim 8, wherein the cardiac repolarization detection processor is further configured to compute a diastolic interval using the depolarization tick time $T_D$ and a an immediately previous repolarization tick time $T_{R-1}$.

* * * * *